US010753235B2

(12) United States Patent
Harris et al.

(10) Patent No.: US 10,753,235 B2
(45) Date of Patent: Aug. 25, 2020

(54) USE OF RECOVERED POWER IN A PROCESS

(71) Applicant: UOP LLC, Des Plaines, IL (US)

(72) Inventors: James W. Harris, Palatine, IL (US); Donald A. Eizenga, Elk Grove Village, IL (US); Michael Van de Cotte, Palatine, IL (US); David A. Wegerer, Lisle, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/924,034

(22) Filed: Mar. 16, 2018

(65) Prior Publication Data

US 2019/0284966 A1  Sep. 19, 2019

(51) Int. Cl.
| F01K 23/06 | (2006.01) |
| F01D 17/16 | (2006.01) |
| F01D 15/10 | (2006.01) |
| H02J 3/46 | (2006.01) |
| H02J 7/00 | (2006.01) |
| C07C 7/04 | (2006.01) |
| B01D 3/14 | (2006.01) |
| C07C 7/08 | (2006.01) |

(52) U.S. Cl.
CPC .............. *F01K 23/064* (2013.01); *B01D 3/14* (2013.01); *C07C 7/04* (2013.01); *C07C 7/08* (2013.01); *F01D 15/10* (2013.01); *F01D 17/16* (2013.01); *H02J 3/46* (2013.01); *H02J 7/0068* (2013.01); *F05D 2220/31* (2013.01); *F05D 2220/62* (2013.01); *F05D 2270/05* (2013.01)

(58) Field of Classification Search
USPC .................... 290/52, 54; 166/244.1
See application file for complete search history.

(56) References Cited

U.S. PATENT DOCUMENTS

| 2,276,714 | A | * | 3/1942 | Brown | ..................... F01D 1/026 |
| | | | | | 415/203 |
| 2,436,683 | A | * | 2/1948 | Wood, Jr. | ................ H02K 5/128 |
| | | | | | 290/43 |
| 4,037,655 | A | * | 7/1977 | Carpenter | ................ E21B 36/00 |
| | | | | | 166/245 |

(Continued)

FOREIGN PATENT DOCUMENTS

| CN | 102203780 A | 9/2011 |
| CN | 103917280 A | 7/2014 |

(Continued)

OTHER PUBLICATIONS

Tsourapas, Vasilios, Control Analysis of Integrated Fuel Cell Systems with Energy Recuperation Devices, 2007.

(Continued)

*Primary Examiner* — Pedro J Cuevas (57) ABSTRACT

Processes and apparatus for recovering energy from a petroleum, petrochemical, or chemical process are disclosed. The process comprises providing a fluid process stream in a petroleum, petrochemical, or chemical process zone having a direct current power input; controlling a flow rate of the process stream by directing at least a portion of the process stream through a first power-recovery turbine to generate electric power as direct current therefrom; and providing the recovered direct current to the direct current power input of the process zone.

20 Claims, 4 Drawing Sheets

(56) References Cited

U.S. PATENT DOCUMENTS

| | | | |
|---|---|---|---|
| 4,057,736 A * | 11/1977 | Jeppson | F01K 13/00 290/1 R |
| 4,285,481 A | 8/1981 | Biscomb | |
| 4,369,373 A * | 1/1983 | Wiseman | E21B 36/04 290/2 |
| 4,387,575 A * | 6/1983 | Wenzel | F02C 1/04 60/648 |
| 4,455,614 A | 6/1984 | Martz et al. | |
| 4,496,845 A * | 1/1985 | Ensign | F03B 15/12 290/43 |
| 5,043,592 A * | 8/1991 | Hochstrasser | F03B 13/00 290/52 |
| 5,209,634 A * | 5/1993 | Owczarek | F01D 25/30 415/150 |
| 5,384,489 A | 1/1995 | Bellac | |
| 5,481,145 A | 1/1996 | Canders et al. | |
| 5,606,858 A * | 3/1997 | Amir | F02C 1/00 60/648 |
| 5,628,191 A * | 5/1997 | Kueck | F02C 1/00 60/655 |
| 5,685,154 A * | 11/1997 | Bronicki | F02C 1/00 60/648 |
| 6,011,334 A * | 1/2000 | Roland | H02K 7/11 290/43 |
| 6,216,463 B1 * | 4/2001 | Stewart | F03G 7/04 210/170.01 |
| 6,265,453 B1 | 7/2001 | Kennedy | |
| 6,354,084 B1 | 3/2002 | McKinley et al. | |
| 6,554,074 B2 * | 4/2003 | Longbottom | E21B 41/0085 166/372 |
| 6,607,030 B2 * | 8/2003 | Bauer | E21B 41/0085 166/65.1 |
| 6,681,155 B1 | 1/2004 | Fujita et al. | |
| 6,820,689 B2 * | 11/2004 | Sarada | E21B 41/0057 166/244.1 |
| 6,824,347 B2 * | 11/2004 | Maloney | E03B 7/075 415/1 |
| 6,898,540 B2 | 5/2005 | Davies | |
| 7,002,261 B2 * | 2/2006 | Cousins | E21B 41/0085 290/43 |
| 7,062,359 B2 | 6/2006 | Bjorklund | |
| 7,141,901 B2 * | 11/2006 | Spring | E21B 4/04 310/77 |
| 7,357,599 B2 * | 4/2008 | Cripps | E03F 3/00 290/1 R |
| 7,452,160 B2 * | 11/2008 | Cripps | E03F 3/00 290/1 R |
| 7,501,712 B2 * | 3/2009 | Bolyard | F03B 13/08 290/43 |
| 7,579,703 B2 * | 8/2009 | Shifrin | F03B 13/105 290/52 |
| 7,608,935 B2 * | 10/2009 | Scherzer | F01K 25/08 290/43 |
| 7,632,040 B2 * | 12/2009 | Cripps | E02B 9/00 290/1 R |
| 7,757,493 B2 | 7/2010 | Bell et al. | |
| 7,768,146 B2 * | 8/2010 | Balzano | F03B 13/00 290/43 |
| 7,802,942 B2 * | 9/2010 | Cripps | E03F 3/00 290/1 R |
| 7,946,789 B2 * | 5/2011 | Cripps | E02B 9/00 290/1 R |
| 7,948,101 B2 | 5/2011 | Burtch | |
| 8,002,499 B2 * | 8/2011 | Cripps | E03F 3/00 290/1 R |
| 8,067,850 B2 * | 11/2011 | Alvarez | B82Y 15/00 290/54 |
| 8,092,675 B2 * | 1/2012 | Kennedy | C02F 1/4674 204/194 |
| 8,147,168 B2 * | 4/2012 | Cripps | E03F 3/00 290/1 R |
| 8,294,292 B2 * | 10/2012 | Irwin | F03B 3/02 290/43 |
| 8,404,918 B2 | 3/2013 | Frey | |
| 8,510,015 B2 | 8/2013 | Beausoleil et al. | |
| 8,680,704 B1 * | 3/2014 | Rooney | F03B 13/02 290/54 |
| 8,763,625 B1 | 7/2014 | Carter | |
| 8,946,921 B2 * | 2/2015 | Kaiser | H02K 7/1823 290/43 |
| 8,967,590 B2 | 3/2015 | Minervini et al. | |
| 8,985,967 B2 * | 3/2015 | Gudivada | F04D 13/043 415/1 |
| 9,085,499 B2 | 7/2015 | Frey et al. | |
| 9,235,228 B2 | 1/2016 | Gazit et al. | |
| 9,677,015 B2 | 6/2017 | Gupta et al. | |
| 9,752,460 B2 | 9/2017 | Bowan | |
| 9,764,272 B2 | 9/2017 | Martin et al. | |
| 9,863,396 B2 * | 1/2018 | Oncale | F03B 3/04 |
| 10,246,645 B2 | 4/2019 | Froehle et al. | |
| 10,260,415 B2 | 4/2019 | Simpkin et al. | |
| 10,508,568 B2 * | 12/2019 | Frey | H02J 3/46 |
| 2004/0011523 A1 * | 1/2004 | Sarada | E21B 41/0057 166/244.1 |
| 2005/0034463 A1 | 2/2005 | Simpson et al. | |
| 2006/0054318 A1 * | 3/2006 | Sarada | E21B 41/0057 166/266 |
| 2006/0056120 A1 | 3/2006 | Kawamura et al. | |
| 2007/0212213 A1 * | 9/2007 | Bolyard | F03B 13/08 415/151 |
| 2008/0015839 A1 | 1/2008 | Noureldin et al. | |
| 2008/0017369 A1 * | 1/2008 | Sarada | E21B 43/40 166/244.1 |
| 2008/0238105 A1 * | 10/2008 | Ortiz | B60K 6/485 290/54 |
| 2008/0290663 A1 * | 11/2008 | Shifrin | F03B 13/105 290/52 |
| 2009/0125152 A1 | 5/2009 | Skowronski et al. | |
| 2010/0019496 A1 * | 1/2010 | Yu | F01D 15/10 290/52 |
| 2010/0154428 A1 * | 6/2010 | Yu | F01K 23/068 60/772 |
| 2010/0301617 A1 * | 12/2010 | Lundbladh | F01D 17/162 290/1 R |
| 2011/0077448 A1 | 3/2011 | Frey | |
| 2011/0100004 A1 | 5/2011 | Al-Mazeedi | |
| 2012/0107227 A1 | 5/2012 | Fischer et al. | |
| 2012/0118526 A1 | 5/2012 | Sudau et al. | |
| 2012/0227440 A1 | 9/2012 | Guidati et al. | |
| 2012/0245754 A1 | 9/2012 | Mehnert | |
| 2012/0260667 A1 | 10/2012 | Chillar et al. | |
| 2012/0326443 A1 * | 12/2012 | Vince | F01D 15/10 290/7 |
| 2013/0019530 A1 | 1/2013 | Favilli et al. | |
| 2013/0199185 A1 | 8/2013 | Wain et al. | |
| 2014/0331672 A1 | 11/2014 | Filippi et al. | |
| 2015/0118131 A1 | 4/2015 | Martin et al. | |
| 2016/0079756 A1 | 3/2016 | Ikeyama et al. | |
| 2016/0141878 A1 | 5/2016 | Johansen | |
| 2016/0161536 A1 | 6/2016 | Amminudin | |
| 2016/0252015 A1 | 9/2016 | Kusumi et al. | |
| 2016/0305396 A1 * | 10/2016 | Oncale | F03B 3/04 |
| 2016/0319198 A1 | 11/2016 | Quanci et al. | |
| 2017/0058206 A1 | 3/2017 | Noureldin et al. | |
| 2017/0058207 A1 | 3/2017 | Noureldin et al. | |
| 2017/0328340 A9 * | 11/2017 | Oncale | F03B 3/04 |
| 2019/0199128 A1 | 6/2019 | Neufeld et al. | |
| 2019/0284962 A1 * | 9/2019 | Frey | F01K 7/165 |
| 2019/0286072 A1 * | 9/2019 | Frey | G05B 13/026 |
| 2019/0288517 A1 * | 9/2019 | Frey | F01D 17/16 |
| 2020/0056509 A1 * | 2/2020 | Frey | F01K 23/064 |

FOREIGN PATENT DOCUMENTS

| | | |
|---|---|---|
| CN | 104463341 A | 3/2015 |
| CN | 206538206 | 10/2017 |
| EP | 0552039 | 7/1993 |
| EP | 2778354 A1 | 9/2014 |
| FR | 2414162 | 8/1979 |

(56) References Cited

FOREIGN PATENT DOCUMENTS

| RU | 2014114067 | | 10/2015 |
|---|---|---|---|
| WO | 2007005036 | A1 | 1/2007 |
| WO | 2007105976 | A1 | 9/2007 |
| WO | 2007105976 | A2 | 9/2007 |
| WO | 2007053036 | A1 | 10/2007 |
| WO | 2012128928 | A1 | 9/2012 |
| WO | 2013148175 | A1 | 10/2013 |
| WO | 2014119569 | A1 | 8/2014 |
| WO | 2014178079 | A2 | 11/2014 |
| WO | 2015065949 | A1 | 5/2015 |
| WO | 2016177376 | A1 | 11/2016 |
| WO | 2018005184 | A1 | 1/2018 |

OTHER PUBLICATIONS

The Elliot Group, Maximize the Efficiency of your Steam Process, 2014.

U.S. Department of Energy, Replace Pressure-Reducing Valves with Backpressure Turbogenerators.

Mechanical Solutions, Inc., Replacing a Pressure Reducing Valve with a Hydro Turbine for a Municipal Water Supply, Jul. 19, 2016.

Frey, Stanley Joseph, et al., U.S. Appl. No. 15/923,990, filed Mar. 16, 2018 and entitled "Turbine with Supersonic Separation".

Frey, Stanley J., et al., U.S. Appl. No. 62/644,086, filed Mar. 16, 2018 and entitled "System for Consolidation and Use of Power Recovered from a Turbine in a Process Unit".

Frey, Stanley J., et al., U.S. Appl. No. 62/644,104, filed Mar. 16, 2018 and entitled "System for Power Recovery from Quench and Dilution Vapor Streams".

Frey, Stanley Joseph, et al., U.S. Appl. No. 15/924,037, filed Mar. 16, 2018 and entitled "Power Recovery from Quench and Dilution Vapor Streams".

Frey, Stanley J., U.S. Appl. No. 15/923,936, filed Mar. 16, 2018 and entitled "Energy-Recovery Turbines for Gas Streams".

Frey, Stanley J., et al., U.S. Appl. No. 15/923,945, filed Mar. 16, 2018 and entitled "Consolidation and Use of Power Recovered from a Turbine in a Process Unit".

Frey, Stanley J., et al., U.S. Appl. No. 15/923,964, filed Mar. 16, 2018 and entitled "Process Improvement through the Addition of Power Recovery Turbine Equipment in Existing Processes".

Frey, Stanley Joseph, et al., U.S. Appl. No. 15/923,997, filed Mar. 16, 2018 and entitled "Processes for Adjusting at Least One Process Condition of a Chemical Processing Unit with a Turbine".

Frey, Stanley Joseph, et al., U.S. Appl. No. 15/923,978, filed Mar. 16, 2018 and entitled "Hydroprocessing Unit with Power Recovery Turbines".

Harris, James W., et al., U.S. Appl. No. 15/923,995, filed Mar. 16, 2018 and entitled "Steam Reboiler with Turbine".

International Search Report from corresponding PCT application No. PCT/US2019/022424, dated May 23, 2019.

Written Opinion from corresponding PCT application No. PCT/US2019/022424, dated May 7, 2019.

Guitiérrez-Antonio, Claudia, et al, Intensification of the hydrotreating process to produce renewable aviation fuel through reactive distillation, Science Direct, vol. 124, Feb. 2018.

Mohammadzadeh, Ashkan, et al., Design of a wind turbine model for clean energy. Case study: Khorasan Razavi regional electricity company, Acta Technica, 62, No. 4B/2017-1-8.

\* cited by examiner

USE OF RECOVERED POWER IN A PROCESS

BACKGROUND

Petroleum, petrochemical, and chemical processing units generally use conventional control valves to control the large liquid and gas streams. The pressure loss and consequent energy loss across the control valve is substantial. The pressure drop across the control valve at the least open position for a stream with a flow rate of 2000 m$^3$/hr could be about 172 kPa (25 psi). This represents almost 100 kW of dissipated power. As a result, the pump must be oversized to account for the energy dissipation, and that energy is lost on a consistent basis. Moreover, a flow sensing element needs to be installed in the system which adds to the installation cost. Finally, the control valve is typically sealed via a packing system to achieve the lower hydrocarbon fugitive emissions regulated by the EPA and other agencies.

Another problem associated with energy consumption in plants is the variable power requirements over time. For example, the energy required for the operation of various process units in the plant is often shared from one process stream to another, with the outside energy provided by a large energy source such as a fired heater. The process thermal energy may not be available for use for a period of time during start-up, and a supplemental energy source may be needed, such as a steam heater. The steam heater places a demand on the utility system that may not be required later during normal operation.

Typically, when power-recovery turbines are installed in process streams in petroleum, petrochemical, and chemical process plants, the power is sent through mechanical means to a driver for a pump or compressor because this generally has a higher efficiency than conversion to electricity through a generator. However, these systems have lower reliability than electrical generators, require that the power recovered matches closely with the power consumed in a single driver, and require a substantial amount of connection equipment in couplings, gears, switchgear, clutches, and the like that have to be located in a limited space. These issues have generally been addressed by generating electrical power at the power recovery point and providing that as fungible power for any driver within the process unit. Where the power recovery is greater than the power consumed within the process unit, it is exported into the higher voltage level on the plant grid. Most major power recovery installations seen to date have utilized this approach.

However, sending power to the plant's power grid presents its own set of difficulties. It requires electric power conditioning, voltage transformation, and frequency regulation. Equipment is now available in the power recovery field that can bring down unit cost to allow economic power recovery at lower power generation sources. When more cost efficient turbines are installed as control elements in process streams, multiple installations may be desirable. However, the power conditioning, transformer, electrical components, and safety equipment to protect the high voltage grid is costly for multiple installations.

In addition, the utility management of many refineries focuses on fuel gas, electricity, steam, and cooling water as distinct costs associated with operations. In techno-economic evaluations these sources are commonly normalized to a fuel gas equivalent cost to compare alternatives. At the design stage, many of these evaluations are done at a single design point. In reality, the plant will operate dynamically, and the operator will benefit from having choices that will allow optimization of each utility source more fully.

Therefore, there is a need for improved energy recovery and use in petroleum, petrochemical, and chemical processing units.

DETAILED DESCRIPTION

This invention is related to increasing the energy efficiency in process units and to minimizing the cost of using power recovery turbines.

Commercial operating systems consider application of turbines to convert kinetic pressure energy of process fluids to electrical energy. In an example system, a high speed generator develops AC current with 650 volts at 700 Hz, which is first converted to 650 volts direct current via a rectifier, and then converted to 3-phase 380/400/480 volt alternating current and synchronized with the electrical grid at 50 or 60 Hz so that the power can be exported and used by various other users on the grid in a distributed fashion. This power conversion requires various electrical system components and as such can be a considerable part of the system cost (e.g. up to $90K for a $200K system).

In a process unit, there are various locations in the process where excess energy may be extracted, but also various points where energy is directly input. As the energy available in the plant is harvested by turbine power generators at various process points, this power can be used directly, stored locally in a battery system for future use, or sold back to the power grid. The utility manager will enable the refinery operator to view these opportunities in a dynamic fashion that allows them to evaluate fully tradeoffs in the cost of electricity.

One aspect of the invention is to minimize the electrical system cost associated with conversion and grid distribution by direct use of the intermediate power, such as by sending the DC current directly to a resistance heater or other power sink (e.g. battery).

The ideal customer will have variable pricing from the electric utility. During low cost periods, the energy available from their energy harvesting turbines can be stored or used. During peak electrical cost time periods, energy can be pulled from the onsite battery storage to avoid this high cost impact. The plant or refinery using this technique will realize a lower overall cost of production.

This approach considers the plant or refinery operations to uncover all potential energy losses including process inefficiencies, as well as energy harvested from pumping and process pressure letdown areas of the plant. These sources of power are currently untapped because the conventional energy audit focuses on electricity, fuel gas, steam, and cooling water.

With the addition of energy harvesting turbines, the plant will be producing energy as soon as fluids start to move around the plant. Using this power directly to initiate a reaction or provide thermal energy to a unit operation can reduce the utility demand during start-up. The adoption of special start-up energy recovery and distribution offers a new tool to achieve the most economical design.

This approach may allow turbine energy harvesting to reduce fired heat use in process units providing both energy cost reductions and additional environmental benefits. It increases the direct transfer of power from a turbine into heat for the process unit via DC. For example, a DC resistance heater can be used to add heat directly to the process where it is needed, reducing the charge heater or reboiler fired heater duty. It can also be used to supply power to electrical heaters that are only used intermittently, such as during start-up.

For example, resistance heating could be used for processes involving endothermic reactions in which heat input is needed to sustain the chemical reactions, such as catalytic reforming processes to produce aromatics or dehydrogenation of paraffins to produce olefins. Heat energy is also needed for process streams in separation processes, such as heat input to reboilers in distillation processes, temperature swing adsorption regeneration. Heat input is also needed for process stream in heat pumping, such as adsorption and absorption heat pumps. Another situation requiring heat input for process streams is to obtain the desired thermal conditions needed for a downstream process, such as the needed inlet feed temperature for a reaction system, or a distillation column.

Energy may be recovered using a turbine in place of, or in parallel with or in series with, a control valve from streams such as quench gas or stripping steam or other such source. This energy can be used directly in a resistance heater to provide thermal heat input to the process and reduce fired heater loads.

In some embodiments, the process for controlling a flow-rate of and recovering energy from a process stream in a processing unit comprises directing a portion of the process stream through one or more variable-resistance power-recovery turbines to control the flowrate of the process stream using a variable nozzle turbine, inlet variable guide vanes, or direct coupled variable electric load, to name a few, to vary the resistance to flow through the turbine.

The resistance to rotation of the variable-resistance turbine can be varied by an external variable load electric circuit which is in a magnetic field from a magnet(s) that is rotating on the turbine. As more load is put on the circuit, there is more resistance to rotation on the turbine. This in turn imparts more pressure drop across the turbine and slows the process stream flow. An algorithm in the device can also calculate the actual flow through the device by measuring the turbine RPM's and the load on the circuit. The resistance to rotation flow can also be varied by variable position inlet guide vanes. In some embodiments, the power will be generated via power-recovery turbines with variable resistance to flow made possible by either guide vanes or variable load on the electrical power generation circuit. An algorithm to calculate actual flow using the guide vanes position, power output and RPM's can be used.

If slow control response of the turbine is an issue, then the use of the turbine is limited to slow responding or "loose" control point applications. A slow responding application is contemplated to have a response time to reach half way (i.e., 50% of a difference) between a new (or target) steady state condition (e.g., temperature, pressure, flow rate) from an original (or starting) steady state condition when the new (or target) condition differs from the original (or stating) condition of at least 10%, of at least one second, or even greater, for example, ten seconds, at least one minute, at least ten minutes, or an hour or more, for half of the change to completed.

One aspect of the invention is a process for recovering energy from a petroleum, petrochemical, or chemical process. In one embodiment, the process comprises providing a fluid process stream in a petroleum, petrochemical, or chemical process zone having a direct current power input; controlling a flow rate of the process stream by directing at least a portion of the process stream through a first power-recovery turbine to generate electric power as direct current therefrom; and providing the recovered direct current to the direct current power input of the process zone.

In some embodiments, the recovered direct current is provided to at least one of a storage battery, a resistance heater, an electric heater, a pump, a compressor, or a fan.

In some embodiments, there are at least two power-recovery turbines. In some embodiments, the recovered direct current from the first and second power-recovery turbines are combined before providing the recovered direct current to the direct current power input of the process zone.

In some embodiments, the recovered direct current is provided to a storage battery, and direct current from the storage battery is provided to at least one of a fan, a pump, a compressor, a fired heater, an electric heater, a resistance heater, or a steam heater.

In some embodiments, information is received from a plurality of pressure reducing devices, the plurality of pressure reducing devices comprising: the first power-recovery turbine; a control valve; or, both; a power loss value or a power generated value is determined for each of the pressure reducing devices; a total power loss value or a total power generated value is determined based upon the power loss values or the power generated values from each of the pressure reducing devices; and, the total power loss value or the total power generated value is displayed on at least one display screen.

In some embodiments, at least one process parameter in the process zone is adjusted based upon the total power loss value or the total power generated value. In some embodiments, after the at least one process parameter has been adjusted, an updated power loss value or an updated power generated value is determined for each of the pressure reducing devices; an updated total power loss value or an updated total power generated value for the process zone is determined based upon the updated power loss values or the updated power generated values from each of the pressure reducing devices; and, the updated total power loss value or the updated total power generated value is displayed on at least one display screen.

In some embodiments, information associated with conditions outside of the process zone is received, wherein the total power loss value or the total power generated value is determined based in part upon the information associated with conditions outside of the process zone.

In some embodiments, information associated with a throughput of the process zone is received, wherein the total power loss value or the total power generated value is determined based in part upon the information associated with the throughput of the process zone. In some embodiments, the throughput of the process zone is maintained while adjusting the at least one process parameter of the portion of a process zone based upon the total power loss value or the total power generated value.

In some embodiments, a portion of the recovered direct current is provided to a central utility grid.

In some embodiments, electric power is provided to the first power-recovery turbine to increase a pressure on a fluid stream. In some embodiments, the electric power is provided to the first power-recover turbine from a central utility grid.

The system could be designed so that the power-recovery turbine has the flexibility to be used either to generate electricity when the pump head is above the required amount or to deliver more energy to the system when additional head is required, such as when optimizing the unit and pushing for maximum production.

In many services, a pump is used to add energy to a fluid so that the fluid can travel from a low pressure vessel to a higher pressure vessel. The general practice is to provide a pump with additional head to increase the fluid pressure to a target pressure that includes the downstream pressure (e.g., a storage tank) and the frictional pressure lost in the piping to the downstream location, as well as an amount for modulating the control valve (e.g., about 25 psi).

In order to increase production, the flow rate of the fluid in the process unit is often increased. However, as the flowrate of the fluid increases, the pump head will decrease. An important concern under these conditions is that the available pump head may be reduced to the point where no further energy is available for the flow controller to vary the flow around the design flowrate. In the industry, this situation is commonly referred as having negative pressure drop in the control valve requiring a modification, such as replacing the pump with one that has higher head for the new highest flowrate condition.

In this situation, the power-recovery turbine could be used to add energy to the fluid stream so that production can be increased without the need to modify the pump to produce more head. When the system is operating at a low flow condition, the pump provides excess head that can be harvested as electricity. As flow rate increases, the excess head will decrease along the pump curve as pump head is a function of flow rate. In situations where the pump does not have sufficient head to achieve the target pressure, the power-recovery turbine can be used to supplement the energy supplied by the pump in order to create the necessary pumping ability.

This approach is particularly applicable in optimization and revamp engineering studies. By utilizing the power-recovery turbine to add energy to the system under certain conditions instead of using the power-recovery turbines only to recover excess energy to generate electricity, the plant could approach much closer to the energy balance point where the minimum amount of energy to move the fluid is used.

Another aspect of the invention is a process for recovering energy from a petroleum, petrochemical, or chemical process. In one embodiment, the process comprises providing a fluid process stream in a petroleum, petrochemical, or chemical process zone having a direct current power input; controlling a flow rate of the process stream by directing at least a portion of the process stream through a first power-recovery turbine to generate electric power as direct current therefrom; providing the recovered direct current to the direct current power input of the petroleum, petrochemical, or chemical process zone; receiving information from a plurality of pressure reducing devices, the plurality of pressure reducing devices comprising: the first power-recovery turbine, a control valve, or both; determining a power loss value or a power generated value for each of the pressure reducing devices; determining a total power loss value or a total power generated value based upon the power loss values or the power generated values from each of the pressure reducing devices; and displaying the total power loss value or the total power generated value on at least one display screen.

In some embodiments, the process further comprising providing electric power to the first power-recovery turbine to increase a pressure on a fluid stream.

Another aspect of the invention is an apparatus for recovering energy in a petroleum, petrochemical, or chemical process. In one embodiment, the apparatus comprises a petroleum, petrochemical, or chemical process zone having a direct current power input; a fluid process stream flowing through the process zone; a variable-resistance power-recovery turbine, a portion of the first process stream flowing through the first power-recovery turbine to generate electric power as direct current therefrom; and a DC bus electrically connected to the power-recovery turbine and to the direct current power input.

In some embodiments, the apparatus further comprises at least one of a resistance heater, a battery storage system, an electric heater, a fired heater, a steam heater, a pump, a compressor, a fan, and wherein the direct current power input is the direct current power input to at least one of the resistance heater or the battery storage system.

In some embodiments, the power-recovery turbines comprise adjustable guide vane power-recovery turbines or variable load power-recovery turbines.

In some embodiments, the process zone comprises at least one of an alkylation zone, a separation zone, an isomerization zone, a catalytic reforming zone, a fluid catalyst cracking zone, a hydrocracking zone, a hydrotreating zone, a hydrogenation zone, a dehydrogenation zone, an oligomerization zone, a desulfurization zone, an alcohol to olefins zone, an alcohol to gasoline zone, an extraction zone, a distillation zone, a sour water stripping zone, a liquid phase adsorption zone, a hydrogen sulfide reduction zone, a transalkylation zone, a coking zone, or a polymerization zone.

Figure 1:
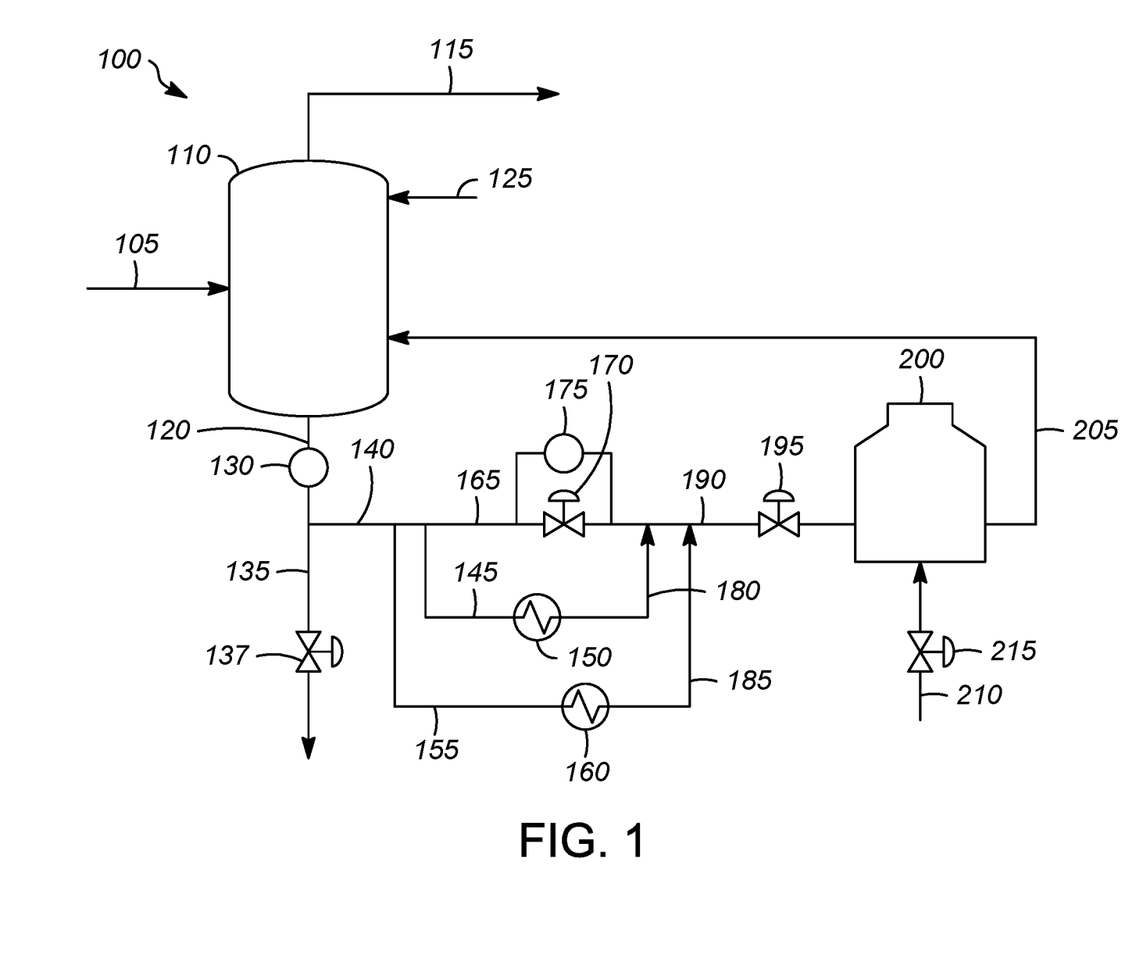
FIG. 1 is an illustration of a portion of an existing process.
Figure 2:
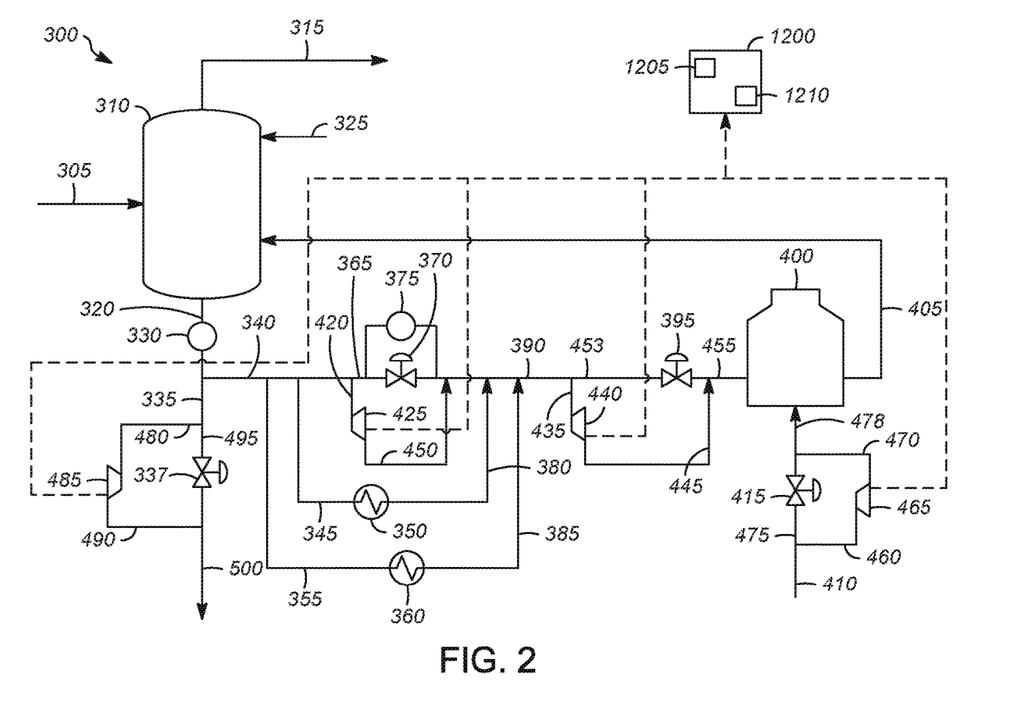
FIG. 2 is an illustration of the same portion of the process of FIG. 1 incorporating the present invention.

FIGS. 1 and 2 illustrate the incorporation of the present invention into a portion of an existing process.

FIG. 1 shows a portion of a xylenes fractionation process 100. Feed 105 is sent to xylene distillation column 110 where it is separated into overhead stream 115 and bottoms stream 120. There is a reflux stream 125 entering near the top of the xylene distillation column 110.

The bottoms stream 120 is sent through pump 130 before being split into streams 135 and 140.

Stream 135 is sent through control valve 137. Stream 135 is sent to a heavy aromatics column (not shown) for further processing, for example.

A first portion 145 of stream 140 is sent through heat exchanger 150, to provide heat for the raffinate column reboiler, and a second portion 155 is sent through heat exchanger 160, to provide heat for the extract column reboiler. The remainder 165 of stream 140 is sent through control valve 170. There is a pressure differential indicating controller 175 to provide driving force to flow the first and second portions 145, 155 of this stream 140 to the additional heat exchangers 150, 160 and return it back downstream after fully utilizing the heat in this circulation of hot bottoms material as thermal energy for the overall process unit from the single xylene column reboiler 200.

Stream 180 from heat exchanger 150 and stream 185 from heat exchanger 160 are combined with the remainder 165, and the combined stream 190 flows through controller 195 to the xylene column reboiler 200. The heated bottoms stream 205 is returned to the bottom of the xylene distillation column 110.

Fuel gas stream 210 is sent through control valve 215 to the xylene column reboiler 200.

FIG. 2 illustrates the addition of power recovery turbines in the xylenes fractionation process 300. Feed 305 is sent to xylene distillation column 310 where it is separated into overhead stream 315 and bottoms stream 320. There is a reflux stream 325 entering near the top of the xylene distillation column 310.

The bottoms stream 320 is sent through pump 330 before being split into streams 335 and 340.

A first portion 345 of stream 340 is sent through heat exchanger 350, and a second portion 355 is sent through heat exchanger 360. A third portion 420 of stream 340 is sent through power-recovery turbine 425 to recover electric power. The remainder 365 of stream 340 is sent through control valve 370. There is a pressure differential indicating controller 375.

Stream 450 from power recovery turbine 425, stream 380 from heat exchanger 350, and stream 385 from heat exchanger 360 are combined with the remainder of 365 to form a combined stream 390. A portion, 435, of the combined stream 390 is sent through power-recovery turbine 440 to recover electric power. The remainder 453 of combined stream 390 is sent through control valve 395.

Stream 445 from power-recovery turbine 440 is combined with the remainder 453 to form combined stream 455 which is sent to the xylene column reboiler 400.

The heated bottoms stream 405 is sent back to the bottom of the xylene distillation column 310.

A portion 460 of fuel gas stream 410 is sent through power recovery turbine 465 to recover electric power. The remainder 475 of 410 is sent to control valve 415. The stream 470 from the power recovery turbine 465 and the remainder 475 of fuel gas stream 410 are combined into combined stream 478 and sent to the xylene column reboiler 400.

A portion 480 of stream 335 is sent through power-recovery turbine 485 to recover electric power. The remainder 495 of stream 335 is sent through control valve 337. Stream 490 from the power-recovery turbine 485 is combined with the remainder 495 to form stream 500. Stream 500 is sent to a heavy aromatics column (not shown) for further processing, for example.

In this illustration, the power recovered from power recovery turbines 425, 440, 465, 485 can be used to provide power 331 to one or more of the pump 330, or additional electric energy users, such as fans, compressor, and pumps associated with the operation, not shown.

An example of suitable power conditioning is described in application Ser. No. 15/923,945, entitled CONSOLIDATION AND USE OF POWER RECOVERED FROM A TURBINE IN A PROCESS UNIT, filed Mar. 16, 2018, which is incorporated herein by reference in its entirety.

In some embodiments, one or more of the power-recovery turbines 425, 440, 465, 485 can also be used to provide head pressure (increase pressure of the stream), such as pump 330.

Figure 3:
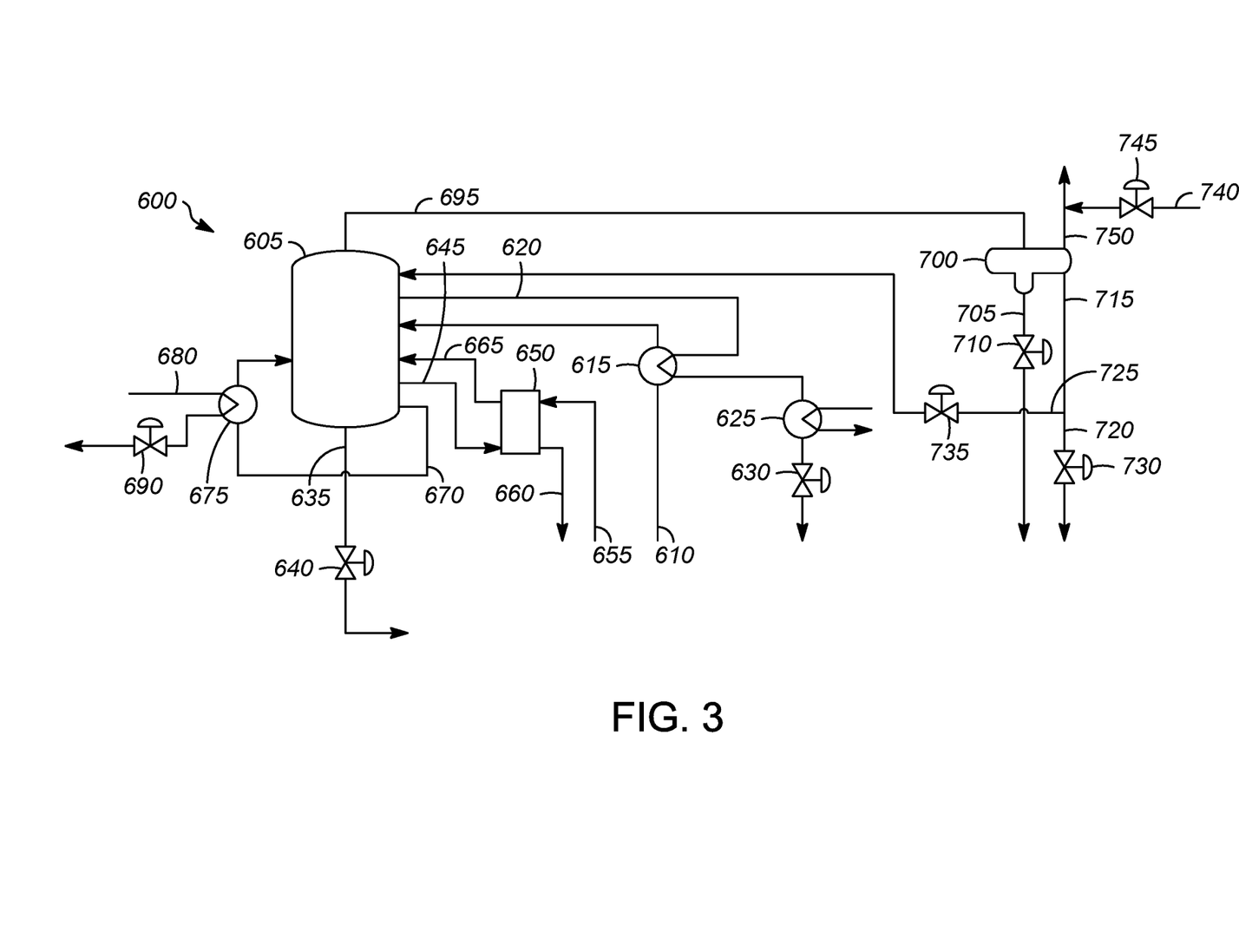
FIG. 3 is an illustration of a portion of another existing process.
Figure 4:
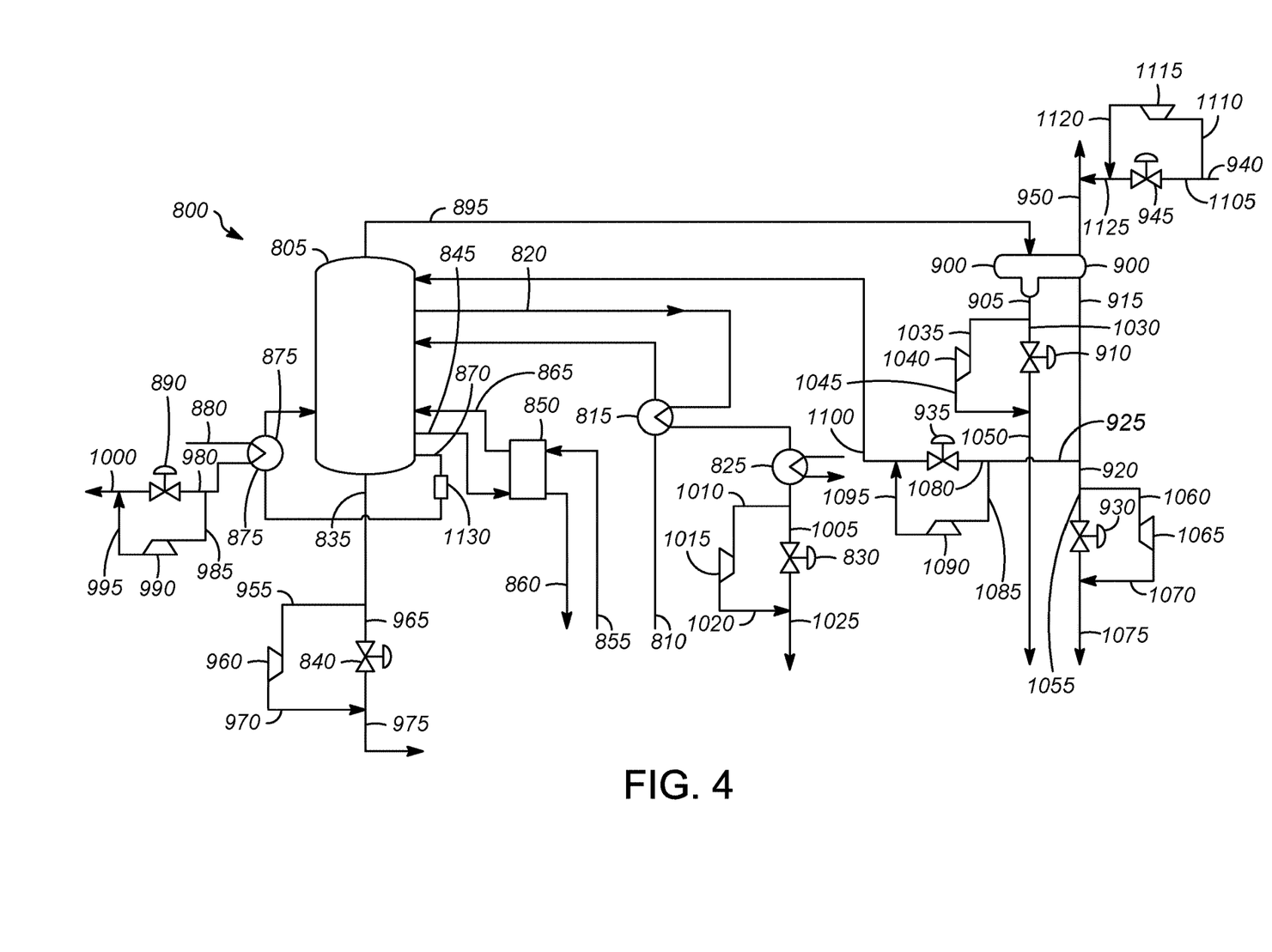
FIG. 4 is an illustration of the same portion of the process of FIG. 3 incorporating the present invention.

FIGS. 3 and 4 illustrate the incorporation of the present invention into a portion of another process.

FIG. 3 illustrates a benzene separation process 600 including a benzene column 605. The feed stream 610 can be extract from an extractive distillation process or a finishing column overhead stream from an adsorptive separation process, for example.

The feed stream 610 is sent to heat exchanger 615 where it is preheated before entering the benzene column 605. The benzene product stream 620 exits the column and exchanges heats with the feed stream 610 in heat exchanger 615. Benzene product stream 620 is further cooled in heat exchanger 625 and sent through control valve 630 to storage (not shown).

Bottoms stream 635 is sent through control valve 640 for further processing in a toluene column (not shown), for example.

A reboiler stream 645 exits the column and is sent to the benzene column reboiler 650 for heating. An overhead vapor stream 655 from an extract column in an adsorptive separation process, for example, can also be sent to the benzene column reboiler 650. A liquid stream 660 from the benzene column reboiler 650 can be sent to an extract column receiver in an adsorptive separation process (not shown). Stream 665 exits the benzene column reboiler 650 and is sent to the benzene column 605.

Stream 670 is sent to a heat exchanger 675 as an auxiliary reboiler and returned to the benzene column 605. Steam stream 680 is sent through heat exchanger 675 to heat stream 670. After exiting the heat exchanger 675, the steam stream 680 flows through a control valve 690.

Benzene column overhead stream 695 is condensed and sent to the benzene column receiver 700. Water stream 705 is sent through control valve 710. Benzene column condensed overhead stream 715 is split into a first part 720 and a second part 725. The first part 720 is sent through control valve 730. The second part 725 is sent through control valve 735 and returned to the benzene column 605, as reflux. Nitrogen stream 740 is sent through control valve 745 and combined with gas stream 750.

FIG. 4 illustrates the addition of power recovery turbines in the benzene separation process 800. The feed stream 810 is sent to heat exchanger 815 where it is preheated before entering the benzene column 805. The benzene product stream 820 exits the column and exchanges heats with the feed stream 810 in heat exchanger 815. Benzene product stream 820 is further cooled in heat exchanger 825. Cooled benzene product stream 820 split into first and second portions 1005, 1010. First portion 1005 flows through a control valve 830. Second portion 1010 is sent through power control turbine 1015. Stream 1020 from the power control turbine 1015 is combined with the first portion 1005 to form benzene product stream 1025.

A first portion 955 of bottoms stream 835 is sent to power recovery turbine 960 to recover power. A second portion 965 of bottoms stream 835 is sent through control valve 840. The second portion 965 is combined with stream 970 from the power recovery turbine 960 to form combined stream 975 which is sent for further processing in a toluene column (not shown), for example.

A reboiler stream 845 exits the column and is sent to the benzene column reboiler 850 for heating. An overhead vapor stream 855 from an extract column in an adsorptive separation process, for example, can also be sent to the benzene column reboiler 850. A liquid stream 860 from the benzene column reboiler 850 can be sent to an extract column receiver in an adsorptive separation process (not shown). Stream 865 exits the benzene column reboiler 850 and is sent to the benzene column 805.

Stream 870 is sent to an auxiliary reboiler 875 after passing through electric heater 1130 and returned to the benzene column 805. Steam stream 880 is sent through auxiliary reboiler 875. After exiting the auxiliary reboiler 875, the steam stream 880 is split into first and second portions, 980 and 985. First portion 980 flows through a control valve 890. Second portion 985 is sent through power control turbine 990. Stream 995 from the power control turbine 990 is combined with the first portion 980 to form stream 1000.

Benzene column overhead stream 895 is condensed and sent to the benzene column receiver 900. Water stream 905 is split into first and second portions 1030 and 1035. First portion 1030 flows through a control valve 910. Second portion 1035 is sent through power control turbine 1040. Stream 1045 from the power control turbine 1040 is combined with the first portion 1030 to form water stream 1050.

Benzene stream 915 is split into a first part 920 and a second part 925. The first part 920 is split into first and second portions 1055 and 1060. First portion 1055 flows through a control valve 930. Second portion 1060 is sent through power control turbine 1065. Stream 1070 from the power control turbine 1065 is combined with the first portion 1055 to form benzene drag stream 1075.

The second part 925 is split into first and second portions 1080, 1085. First portion 1080 flows through a control valve 935. Second portion 1085 is sent through power control turbine 1090. Stream 1095 from the power control turbine 1090 is combined with the first portion 1080 to form stream 1100 which is returned to the benzene column 805.

Nitrogen stream 940 is split into first and second portions 1105 and 1110. First portion 1105 flows through a control valve 945. Second portion 1110 is sent through power control turbine 1115. Stream 1120 from the power control turbine 1115 is combined with the first portion 1105 to form stream 1125 which is combined with gas stream 950.

An electric heater 1130 can be added on stream 870. The power recovered from power control turbines 1015, 960, 990, 1090, 1040, 1115, 1065 can be used to reduce the steam requirements for the auxiliary reboiler 875. The energy supplied to the electric heater from the power control turbines 1015, 960, 990, 1090, 1040, 1115, 1065 increases the inlet temperature to this reboiler, resulting in less steam needed to provide the desired temperature exiting the auxiliary reboiler, reducing the utility cost to the owner for steam consumption.

As would be understood by those of skill in the art, one or more additional power recovery turbines can be added to the process where control valves are in place in order to recover power which can then be sent to one or more pieces of equipment which require power input, such as are described above.

The devices and processes of the present invention are contemplated as being utilized in a petroleum, petrochemical, or chemical process zone. As is known, such petroleum, petrochemical, or chemical process zones utilize a process control system, typically on a computer in a control center.

The process control system described in connection with the embodiments disclosed herein may be implemented or performed on the computer with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, or, the processor may be any conventional processor, controller, microcontroller, or state machine. A processor may also be a combination of computing devices, e.g., a combination of a DSP and a microprocessor, two or more microprocessors, or any other combination of the foregoing.

The steps of the processes associated with the process control system may be embodied in an algorithm contained directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is in communication with the processor such the processor reads information from, and writes information to, the storage medium. This includes the storage medium being integral to or with the processor. The processor and the storage medium may reside in an ASIC. The ASIC may reside in a user terminal. Alternatively, the processor and the storage medium may reside as discrete components in a user terminal. These devices are merely intended to be exemplary, non-limiting examples of a computer readable storage medium. The processor and storage medium or memory are also typically in communication with hardware (e.g., ports, interfaces, antennas, amplifiers, signal processors, etc.) that allow for wired or wireless communication between different components, computers processors, or the like, such as between the input channel, a processor of the control logic, the output channels within the control system and the operator station in the control center.

In communication relative to computers and processors refers to the ability to transmit and receive information or data. The transmission of the data or information can be a wireless transmission (for example by Wi-Fi or Bluetooth) or a wired transmission (for example using an Ethernet RJ45 cable or an USB cable). For a wireless transmission, a wireless transceiver (for example a Wi-Fi transceiver) is in communication with each processor or computer. The transmission can be performed automatically, at the request of the computers, in response to a request from a computer, or in other ways. Data can be pushed, pulled, fetched, etc., in any combination, or transmitted and received in any other manner.

According to the present invention, therefore, it is contemplated that the process control system receives information from the power recovery turbines 425, 440, 465, 485 relative to an amount of electricity generated by the power recovery turbines 425, 440, 465, 485. It is contemplated that the power recovery turbines 425, 440, 465, 485 determine (via the processor) the amount of electricity it has generated. Alternatively, the process control system receiving the information determines the amount of electricity that has been generated by the power recovery turbines 425, 440, 465, 485. In either configuration, the amount of the electricity generated by the power recovery turbines 425, 440, 465, 485 is displayed on at least one display screen associated with the computer in the control center. If the petroleum, petrochemical, or chemical process zone comprises a plurality of power recovery turbines 425, 440, 465, 485, it is further contemplated that the process control system receives information associated with the amount of electricity generated by each of the power recovery turbines 425, 440, 465, 485. The process control system determines a total electrical power generated based upon the information associated with the each of the power recovery turbines 425, 440, 465, 485 and displays the total electrical power generated on the display screen. The total electrical power generated may be displayed instead of, or in conjunction with, the amount of electrical power generated by the individual power recovery turbines 425, 440, 465, 485.

As discussed above, the electrical energy recovered by the power recovery turbines 425, 440, 465, 485 is often a result of removing energy from the streams that was added to the streams in the petroleum, petrochemical, or chemical process zone. Thus, it is contemplated that the processes according to the present invention provide for the various processing conditions associated with the petroleum, petrochemical, or chemical process zone to be adjusted into order to lower the energy added to the stream(s). The parallel control valves installed near each turbine could first be balanced by adjusting each turbine to recover more power while decreasing the flow from the associated control valve to maintain the same flow with higher energy recovery from the turbine. As this optimization is accomplished the additional power could be stored for future use, directed to the electric heater, 1130, as described or directed to other electrically driven equipment such as cooling fans or pumps, not shown.

It is contemplated that the process control system receives information associated with the throughput of the petroleum, petrochemical, or chemical process zone, and determines a target electrical power generated value for the turbine(s) since the electricity represents energy that is typically added to the overall petroleum, petrochemical, or chemical process zone. The determination of the target electrical power generated value may be done when the electricity is at or near a predetermined level. In other words, if the amount of electricity produced meets or exceeds a predetermined level, the process control system can determine one or more processing conditions to adjust and lower the amount of electricity generated until it reaches the target electrical power generated value.

Thus, the process control system will analyze one or more changes to the various processing conditions associated with the petroleum, petrochemical, or chemical process zone to lower the amount of energy recovered by the turbines of the petroleum, petrochemical, or chemical process zone. Preferably, the processing conditions are adjusted without adjusting the throughput of the petroleum, petrochemical, or chemical process zone. This allows for the petroleum, petrochemical, or chemical process zone to have the same throughput, but with a lower operating cost associated with the same throughput. The process control software may calculate and display the difference between the target electrical power generated value and the total electrical power generated on the display screen.

For example, the process control software may recognize that the total electrical power generated exceeds a predetermined level. Accordingly, the process control software may determine the target electrical power generated value. Based upon other data and information received from other sensors and data collection devices typically associated with the petroleum, petrochemical, or chemical process zone, the process control software may determine that the amount of fuel consumed in a piece of equipment can be lowered. While maintaining the throughput of the petroleum, petrochemical, or chemical process zone, the amount of fuel consumed in the piece of equipment is lowered. While this may lower the electricity generated by the turbine, the lower fuel consumption provides a lower operating cost for the same throughput.

Thus, not only does the present invention convert energy that is typically lost into a form that is used elsewhere in the petroleum, petrochemical, or chemical process zone, the petroleum, petrochemical, or chemical process zone is provided with opportunities to lower the energy input associated with the overall petroleum, petrochemical, or chemical process zone and increase profits by utilizing more energy efficient processes.

It should be appreciated and understood by those of ordinary skill in the art that various other components, such as valves, pumps, filters, coolers, etc., are not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Specific Embodiments

While the following is described in conjunction with specific embodiments, it will be understood that this description is intended to illustrate and not limit the scope of the preceding description and the appended claims.

A first embodiment of the invention is a process for recovering energy from a petroleum, petrochemical, or chemical process comprising providing a fluid process stream in a petroleum, petrochemical, or chemical process zone having a direct current power input; controlling a flow rate of the process stream by directing at least a portion of the process stream through a first power-recovery turbine to generate electric power as direct current therefrom; providing the recovered direct current to the direct current power input of the petroleum, petrochemical, or chemical process zone. An embodiment of the invention is one, any or all of prior embodiments in this paragraph up through the first embodiment in this paragraph wherein providing the recovered direct current to the direct current power input of the process zone comprises providing the recovered direct current to at least one of a storage battery, a resistance heater, an electric heater, a pump, a compressor, or a fan. An embodiment of the invention is one, any or all of prior embodiments in this paragraph up through the first embodiment in this paragraph wherein there are at least two power-recovery turbines. An embodiment of the invention is one, any or all of prior embodiments in this paragraph up through the first embodiment in this paragraph further comprising combining the recovered direct current from the first and second power-recovery turbines before providing the recovered direct current to the direct current power input of the process zone. An embodiment of the invention is one, any or all of prior embodiments in this paragraph up through the first embodiment in this paragraph wherein the recovered direct current is provided to a storage battery, and further comprising providing direct current from the storage battery to at least one of a fan, a pump, a compressor, an electric heater, or a resistance heater. An embodiment of the invention is one, any or all of prior embodiments in this paragraph up through the first embodiment in this paragraph further comprising receiving information from a plurality of pressure reducing devices, the plurality of pressure reducing devices comprising the first power-recovery turbine, a control valve, or both; determining a power loss value or a power generated value for each of the pressure reducing devices; determining a total power loss value or a total power generated value based upon the power loss values or the power generated values from each of the pressure reducing devices; and, displaying the total power loss value or the total power generated value on at least one display screen. An embodiment of the invention is one, any or all of prior embodiments in this paragraph up through the first embodiment in this paragraph further comprising adjusting at least one process parameter in the process zone based upon the total power loss value or the total power generated value. An embodiment of the invention is one, any or all of prior embodiments in this paragraph up through the first embodiment in this paragraph further comprising after the at least one process parameter has been adjusted, determining an updated power loss value or an updated power generated value for each of the pressure reducing devices; determining an updated total power loss value or an updated total power generated value for the process zone based upon the updated power loss values or the updated power generated values from each of the pressure reducing devices; and, displaying the updated total power loss value or the updated total power generated value on at least one display screen. An embodiment of the invention is one, any or all of prior embodiments in this paragraph up through the first embodiment in this paragraph further comprising receiving information associated with conditions outside of the process zone, wherein the total power loss value or the total power generated value is determined based in part upon the information associated with conditions outside of the process zone. An embodiment of the invention is one, any or all of prior embodiments in this paragraph up through the first embodiment in this paragraph further comprising receiving information associated with a throughput of the process zone, wherein the total power loss value or the total power generated value is determined based in part upon the information associated with the throughput of the process zone. An embodiment of the invention is one, any or all of prior embodiments in this paragraph up through the first embodiment in this paragraph further comprising maintaining the throughput of the process zone while adjusting the at least one process parameter of the portion of a process zone based upon the total power loss value or the total power generated value. An embodiment of the invention is one, any or all of prior embodiments in this paragraph up through the first embodiment in this paragraph further comprising providing a portion of the recovered direct current to a central utility grid. An embodiment of the invention is one, any or all of prior embodiments in this paragraph up through the first embodiment in this paragraph further comprising providing electric power to the first power-recovery turbine to increase a pressure on a fluid stream. An embodiment of the invention is one, any or all of prior embodiments in this paragraph up through the first embodiment in this paragraph wherein the electric power is provided to the first power-recover turbine from a central utility grid.

A second embodiment of the invention is a process for recovering energy from a petroleum, petrochemical, or chemical process comprising providing a fluid process stream in a petroleum, petrochemical, or chemical process zone having a direct current power input; controlling a flow rate of the process stream by directing at least a portion of the process stream through a first power-recovery turbine to generate electric power as direct current therefrom; providing the recovered direct current to the direct current power input of the petroleum, petrochemical, or chemical process zone; receiving information from a plurality of pressure reducing devices, the plurality of pressure reducing devices comprising the first power-recovery turbine, a control valve, or both; determining a power loss value or a power generated value for each of the pressure reducing devices; determining a total power loss value or a total power generated value based upon the power loss values or the power generated values from each of the pressure reducing devices; and, displaying the total power loss value or the total power generated value on at least one display screen. An embodiment of the invention is one, any or all of prior embodiments in this paragraph up through the second embodiment in this paragraph further comprising providing electric power to the first power-recovery turbine to increase a pressure on a fluid stream.

A third embodiment of the invention is an apparatus for recovering energy in a petroleum, petrochemical, or chemical process comprising a petroleum, petrochemical, or chemical process zone having a direct current power input; a fluid process stream flowing through the process zone; a variable-resistance power-recovery turbine, a portion of the first process stream flowing through the first power-recovery turbine to generate electric power as direct current therefrom; and a DC bus electrically connected to the power-recovery turbine and to the direct current power input. An embodiment of the invention is one, any or all of prior embodiments in this paragraph up through the third embodiment in this paragraph further comprising at least one of a resistance heater, a battery storage system, an electric heater, a pump, a compressor, a fan, and wherein the direct current power input is the direct current power input to at least one of the resistance heater or the battery storage system. An embodiment of the invention is one, any or all of prior embodiments in this paragraph up through the third embodiment in this paragraph wherein the power-recovery turbines comprise adjustable guide vane power-recovery turbines or variable load power-recovery turbines. An embodiment of the invention is one, any or all of prior embodiments in this paragraph up through the third embodiment in this paragraph wherein the process zone comprises at least one of an alkylation zone, a separation zone, an isomerization zone, a catalytic reforming zone, a fluid catalyst cracking zone, a hydrocracking zone, a hydrotreating zone, a hydrogenation zone, a dehydrogenation zone, an oligomerization zone, a desulfurization zone, an alcohol to olefins zone, an alcohol to gasoline zone, an extraction zone, a distillation zone, a sour water stripping zone, a liquid phase adsorption zone, a hydrogen sulfide reduction zone, a transalkylation zone, a coking zone, or a polymerization zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for recovering energy from a petroleum, petrochemical, or chemical process comprising:
   providing a fluid process stream in a petroleum, petrochemical, or chemical process zone in the petroleum, petrochemical, or chemical plant wherein the process zone comprises at least one of an alkylation zone, a separation zone, an isomerization zone, a catalytic reforming zone, a fluid catalyst cracking zone, a hydrocracking zone, a hydrotreating zone, a hydrogenation zone, a dehydrogenation zone, an oligomerization zone, a desulfurization zone, an alcohol to olefins zone, an alcohol to gasoline zone, a petroleum extraction zone, a petrochemical extraction zone, a chemical extraction zone, a distillation zone, a sour water stripping zone, a liquid phase adsorption zone, a hydrogen sulfide reduction zone, a transalkylation zone, a coking zone, or a polymerization zone;

controlling a flow rate of the process stream by directing at least a portion of the process stream through a first variable resistance power-recovery turbine to generate electric power as direct current therefrom;

providing the recovered direct current to at least one of a storage battery, a resistance heater, an electric heater, a pump, a compressor, or a fan in the petroleum, petrochemical, or chemical process zone; and wherein the fluid process stream is used in the petroleum, petrochemical, or chemical process and is not consumed in the first power-recovery turbine.

2. The process of claim 1 wherein there are at least two power-recovery turbines.

3. The process of claim 2 further comprising combining the recovered direct current from the first and second power-recovery turbines before providing the recovered direct current to the at least one of the storage battery, the resistance heater, the electric heater, the pump, the compressor, or the fan.

4. The process of claim 1 wherein the recovered direct current is provided to the storage battery, and further comprising:

providing direct current from the storage battery to at least one of the fan, the pump, the compressor, the electric heater, or the resistance heater.

5. The process of claim 1 further comprising:

receiving information from a plurality of pressure reducing devices, the plurality of pressure reducing devices comprising: the first power-recovery turbine, a control valve, or both, using a process control system including a computer;

determining a power loss value or a power generated value for each of the pressure reducing devices from the amount of electricity each of the pressure reducing devices produced using the process control system;

determining a total power loss value or a total power generated value based upon the power loss values or the power generated values from each of the pressure reducing devices using the process control system; and, displaying the total power loss value or the total power generated value on at least one display screen.

6. The process of claim 5 further comprising adjusting at least one process parameter in the process zone based upon the total power loss value or the total power generated value.

7. The process of claim 6 further comprising:

after the at least one process parameter has been adjusted, determining an updated power loss value or an updated power generated value for each of the pressure reducing devices;

determining an updated total power loss value or an updated total power generated value for the process zone based upon the updated power loss values or the updated power generated values from each of the pressure reducing devices; and, displaying the updated total power loss value or the updated total power generated value on at least one display screen.

8. The process of claim 5 further comprising:

receiving information associated with conditions outside of the process zone, wherein the total power loss value or the total power generated value is determined based in part upon the information associated with conditions outside of the process zone.

9. The process of claim 5 further comprising:

receiving information associated with a throughput of the process zone, wherein the total power loss value or the total power generated value is determined based in part upon the information associated with the throughput of the process zone.

10. The process of claim 9 further comprising:

maintaining the throughput of the process zone while adjusting the at least one process parameter of the portion of a process zone based upon the total power loss value or the total power generated value.

11. The process of claim 1 further comprising:

converting a portion of the recovered direct current to alternating current; and providing the converted alternating current to a central utility grid.

12. The process of claim 1 further comprising providing electric power to the first power-recovery turbine to increase a pressure on a fluid stream.

13. The process of claim 12 wherein the electric power is provided to the first power-recover turbine from a central utility grid.

14. The process of claim 1 wherein the process zone comprises at least one of the alkylation zone, the separation zone, the isomerization zone, the catalytic reforming zone, the fluid catalyst cracking zone, the hydrocracking zone, the hydrotreating zone, the hydrogenation zone, the dehydrogenation zone, the oligomerization zone, the desulfurization zone, the alcohol to olefins zone, the alcohol to gasoline zone, the distillation zone, the sour water stripping zone, the liquid phase adsorption zone, the hydrogen sulfide reduction zone, the transalkylation zone, the coking zone, or the polymerization zone.

15. A process for recovering energy from a petroleum, petrochemical, or chemical process comprising:

providing a fluid process stream in a petroleum, petrochemical, or chemical process zone in the petroleum, petrochemical, or chemical plant wherein the process zone comprises at least one of an alkylation zone, a separation zone, an isomerization zone, a catalytic reforming zone, a fluid catalyst cracking zone, a hydrocracking zone, a hydrotreating zone, a hydrogenation zone, a dehydrogenation zone, an oligomerization zone, a desulfurization zone, an alcohol to olefins zone, an alcohol to gasoline zone, a petroleum extraction zone, a petrochemical extraction zone, a chemical extraction zone, a distillation zone, a sour water stripping zone, a liquid phase adsorption zone, a hydrogen sulfide reduction zone, a transalkylation zone, a coking zone, or a polymerization zone;

controlling a flow rate of the process stream by directing at least a portion of the process stream through a first variable resistance power-recovery turbine to generate electric power as direct current therefrom;

providing the recovered direct current to at least one of a storage battery, a resistance heater, an electric heater, a pump, a compressor, or a fan in the petroleum, petrochemical, or chemical process zone;

receiving information from a plurality of pressure reducing devices, the plurality of pressure reducing devices comprising: the first power-recovery turbine, a control valve, or both;

determining a power loss value or a power generated value for each of the pressure reducing devices;

determining a total power loss value or a total power generated value based upon the power loss values or the power generated values from each of the pressure reducing devices;

displaying the total power loss value or the total power generated value on at least one display screen; and wherein the fluid process stream is used in the petroleum, petrochemical, or chemical process and is not consumed in the first power-recovery turbine.

16. The process of claim 15 further comprising providing electric power to the first power-recovery turbine to increase a pressure on a fluid stream.

17. The process of claim 15 wherein the process zone comprises at least one of the alkylation zone, the separation zone, the isomerization zone, the catalytic reforming zone, the fluid catalyst cracking zone, the hydrocracking zone, the hydrotreating zone, the hydrogenation zone, the dehydrogenation zone, the oligomerization zone, the desulfurization zone, the alcohol to olefins zone, the alcohol to gasoline zone, the distillation zone, the sour water stripping zone, the liquid phase adsorption zone, the hydrogen sulfide reduction zone, the transalkylation zone, the coking zone, or the polymerization zone.

18. An apparatus for recovering energy in a petroleum, petrochemical, or chemical process comprising:

a petroleum, petrochemical, or chemical process zone in the petroleum, petrochemical, or chemical plant wherein the process zone comprises at least one of an alkylation zone, a separation zone, an isomerization zone, a catalytic reforming zone, a fluid catalyst cracking zone, a hydrocracking zone, a hydrotreating zone, a hydrogenation zone, a dehydrogenation zone, an oligomerization zone, a desulfurization zone, an alcohol to olefins zone, an alcohol to gasoline zone, a petroleum extraction zone, a petrochemical extraction zone, a chemical extraction zone, a distillation zone, a sour water stripping zone, a liquid phase adsorption zone, a hydrogen sulfide reduction zone, a transalkylation zone, a coking zone, or a polymerization zone;

a fluid process stream flowing through the process zone;

a variable-resistance power-recovery turbine, a portion of the first process stream flowing through the first power-recovery turbine to generate electric power as direct current therefrom, wherein the first power-recovery turbine does not consume the fluid process stream; and a DC bus electrically connected to the power-recovery turbine and to at least one of a storage battery system, a resistance heater, an electric heater, a pump, a compressor, or a fan in the petroleum, petrochemical, or chemical process zone.

19. The apparatus of claim 18 wherein the power-recovery turbines comprise adjustable guide vane power-recovery turbines or variable load power-recovery turbines.

20. The apparatus of claim 18 wherein the process zone comprises at least one of the alkylation zone, the separation zone, the isomerization zone, the catalytic reforming zone, the fluid catalyst cracking zone, the hydrocracking zone, the hydrotreating zone, the hydrogenation zone, the dehydrogenation zone, the oligomerization zone, the desulfurization zone, the alcohol to olefins zone, the alcohol to gasoline zone, the distillation zone, the sour water stripping zone, the liquid phase adsorption zone, the hydrogen sulfide reduction zone, the transalkylation zone, the coking zone, or the polymerization zone.

* * * * *